United States Patent [19]

Tomizawa et al.

[11] Patent Number: 4,655,085
[45] Date of Patent: Apr. 7, 1987

[54] TRACKLESS SCANNER

[75] Inventors: Fumio Tomizawa, Hitachi; Kenji Tsuchita, Hitachiota; Sakae Sugiyama, Ibaraki, all of Japan

[73] Assignee: Hitachi, Ltd., Tokyo, Japan

[21] Appl. No.: 759,288

[22] Filed: Jul. 26, 1985

[30] Foreign Application Priority Data

Jul. 27, 1984 [JP] Japan .................... 59-155196

[51] Int. Cl.⁴ .......................................... G01N 29/04
[52] U.S. Cl. ..................................................... 73/638
[58] Field of Search ............... 73/638, 637, 640, 622;
324/261; 376/245, 249, 252

[56] References Cited

U.S. PATENT DOCUMENTS 4,531,413 7/1985 Tsuchita et al. ..................... 73/638

FOREIGN PATENT DOCUMENTS 58-129253 8/1983 Japan .

OTHER PUBLICATIONS

"Automated Pipe Scanner for Nuclear Power Plants" from the 1984 National Topical Meeting on Robotics and Remote Handling in Hostile Environments, pp. 181–187.

Primary Examiner—Stephen A. Kreitman
Attorney, Agent, or Firm—Beall Law Offices

[57] ABSTRACT

A trackless scanner for examination of pipings comprises an annular base removably mountable to a plant pipe to be examined, and a plurality of drive wheels for running supported on the base and being in contact with the plant pipe. Each of the drive wheels is associated with a sensor for detecting an angle which the annular base makes when it turns circumferentially of the pipe, a mechanism responsive to a detection signal from the sensor to control the axial running of the drive wheel for running, and a sensor for detecting a curvature of the pipe.

14 Claims, 24 Drawing Figures

MOVING DIRECTION
(FORWARD)    $\epsilon_\theta \fallingdotseq 0$ $\epsilon_\theta < 0$ $\epsilon_\theta > 0$

TRACKLESS SCANNER

BACKGROUND OF THE INVENTION

This invention relates to a scanner used for ultrasonic inspection of pipings in a system such as an atomic power plant, and more particularly to an improvement of a trackless scanner which need not travel on any tracks for its movement, the improvement being such that the trackless scanner can be prevented from being deviated circumferentially of a piping so as to stably scan straight and curved pipe portions.

Japanese Patent Unexamined Publication No. 58-129253 discloses a prior art scanner adapted for scanning straight and curved pipe portions. This prior art scanner has curvature detectors located before and behind a drive wheel which runs in an axial direction of a piping. A curvature of the piping is measured from amounts of expansion and contraction of these curvature detectors and used for controlling posture of the scanner such that the scanner can travel along the straight and curved pipe portions. The scanner of this prior art is efficient to travel in the axial direction of a piping to be examined but due to lack of a function to detect deviated turning of the scanner about the piping axis and a means for preventing the circumferential deviation, this scanner is liable to travel along the surface of the piping spirally or in a snaking fashion including alternate clockwise or rightward and counterclockwise or leftward turnings. This circumferential turning of the scanner is considered to be attributable to a complicatedly related interaction between clearance for a shaft of the drive wheel, accuracy of mounting the drive wheel and unevenness of ground pressure of the drive wheel. When a piping to be examined consists of only horizontally laid pipes, the circumferential turning can be avoided to some extent by mounting the scanner so that its center of gravity is below the bottom side of the pipe. However, any devices adapted for preventing the circumferential turning of a scanner employed for a piping laid three dimensionally in the three-dimensional space have not yet been developed.

SUMMARY OF THE INVENTION

An object of this invention is to provide a trackless scanner which can travel in parallel with a center line (without turning about the center line) of a piping to be examined which is laid three dimensionally.

To accomplish the above object, according to one aspect of the present invention, a trackless scanner comprises an annular base removably mountable to a pipe to be examined, a plurality of drive wheels for running supported on the base and being in contact with the pipe, a sensor, associated with each drive wheel, for detecting a circumferential turning of the base relative to the pipe, a circumferential posture control mechanism, associated with each drive wheel, responsive to a detection signal from the sensor so as to control an axial running of the drive wheel, and a sensor, associated with each drive wheel, for detecting a curvature of the pipe.

The annular base is not always limited to be geometrically circular but it may take any configurations, with cuttings if necessary, which surround the pipe to be examined.

DESCRIPTION OF THE PREFERRED EMBODIMENTS

Figure 1:
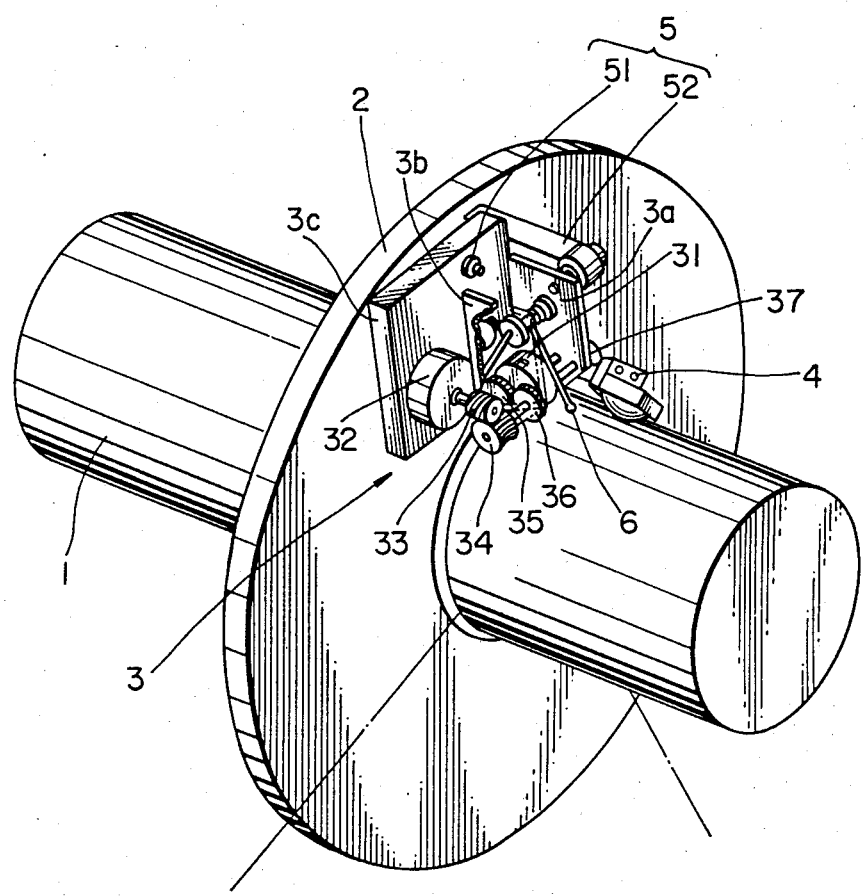
FIG. 1 is a perspective view showing an axial running unit of a scanner according to an embodiment of the invention.
Figure 2:
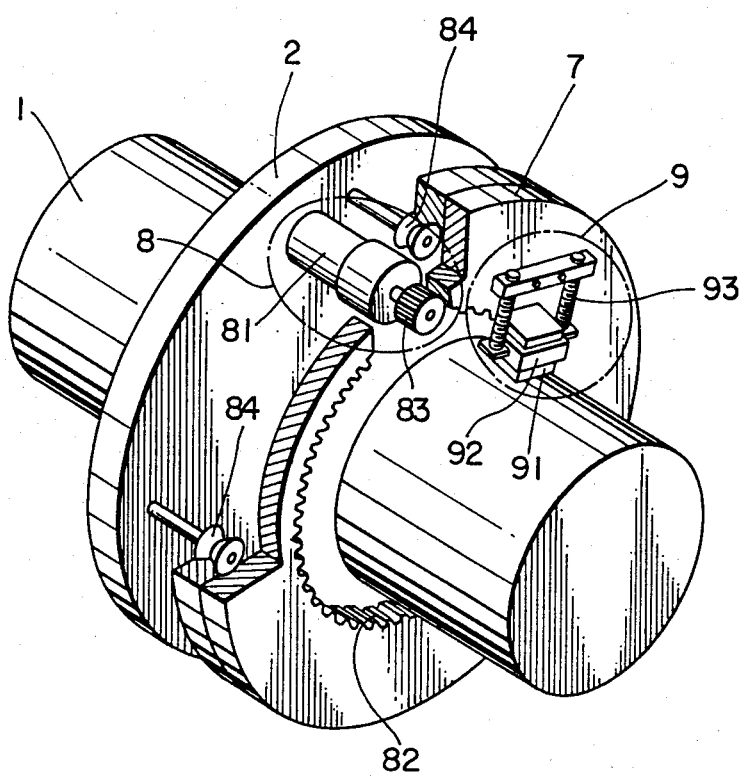
FIG. 2 is a perspective view of a circumferential running unit used in the embodiment of FIG. 1.

Referring now to FIGS. 1 to 5, a trackless scanner according to an embodiment of the invention will be described, of which a unit for axial running is particularly illustrated, in perspective view form, in FIG. 1 and a unit for circumferential rotation is particularly illustrated, also in perspective view form, in FIG. 2.

The scanner exemplified herein comprises a doughnut-like base 2 which is divided into two portions, for example, for removal mounting and which surrounds a pipe 1 to be examined, and a plurality of axial running units 3 each mounted to the base 2 and having a drive wheel 31 which is in contact with an outer peripheral surface of pipe 1 for rotation thereon.

In this embodiment, the scanner has three axial running units 3 arranged circumferentially symmetrically to surround the pipe 1 but for simplicity of illustration, only one unit is depicted in FIG. 1.

The scanner further comprises a snaking prevention sensor 4 fixed to the base 2 and adapted to detect a circumferential turning of the scanner, a circumferential posture control mechanism 5 responsive to a detection signal from the snaking prevention sensor 4 to change the direction of the axial running unit 3, a curvature sensor 6 supported by mount plates 3a and 3b of the axial running unit 3 so as to stride over the drive wheel 31, and a circumferential running unit having a circumferential rotor 7 rotatable with respect to the base 2, as shown in FIG. 2, a circumferential rotor drive mechanism 8 and an ultrasonic probe mechanism 9 fixed to the circumferential rotor 7 and having an ultrasonic probe 91. The three axial running units 3 in this embodiment are arranged circumferentially at 120° intervals.

As shown in FIG. 1, the axial running unit 3 includes an axial drive motor 32 fixed to the mount plate 3c, an input worm gear 33 driven by the motor 32, an output worm gear 34 supported by the mount plate 3b, reduction gears 35 and 36 driven by the output worm gear 34, the drive wheel 31 connected to the reduction gear and supported by the mount plate 3a, and a speed encoder 37 mounted to the mount plate 3a. The mount plates 3a and 3b are fixed to the mount plate 3c. The axial drive motor 32 is controlled so as to cause the scanner to travel axially. The circumferential rotor drive mechanism 8 (FIG. 2) includes a circumferential rotor drive motor 81 fixed to the base 2, a drive gear 83 in mesh with an inner gear 82 of the circumferential rotor 7, and a plurality of guide rollers 84 fixed to the base 2 and arranged circumferentially. The circumferential rotor drive motor 81 is controlled so as to cause the rotor 7 slidably supported by the rollers 84 to rotate relative to the base 2. The ultrasonic probe mechanism 9 fixed to the circumferential rotor 7 has the ultrasonic probe 91 which is normally pushed against the pipe in a diameterical direction thereof or normal thereto by means of a gimbal mechanism 92 and an ultrasonic probe biasing mechanism 93.

Figure 3:
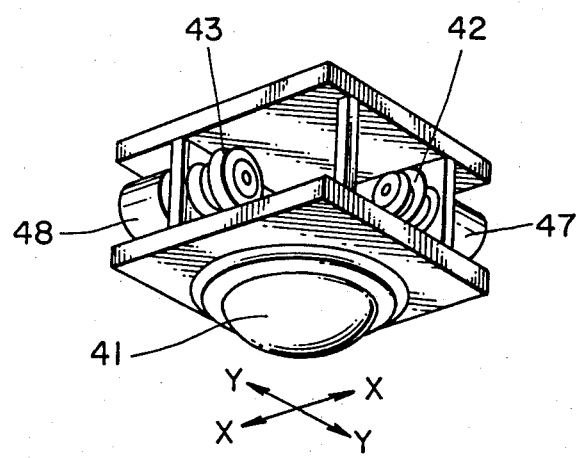
FIG. 3 is a perspective view showing an example of a snaking prevention sensor.

FIG. 3 shows an embodiment of the snaking prevention sensor 4. This sensor has a ball 41 which is in contact with the outer surface of the pipe 1. Upon rotation of the ball 41, rollers 42 and 43 arranged orthogonally with each other detect a Y-axis component standing for the circumferential direction and an X-axis component standing for the axial direction, respectively. Amounts of detected X-axis and Y-axis components are converted respectively by encoders 47 and 48 into electrical quantities. If the scanner turns circumferentially, the Y-axis component of the snaking prevention sensor 4 takes place, thus providing an amount of turning. The X-axis components indicative of amounts of axial travel of the scanner may be integrated to measure a scanning position referenced to a start point.

Figure 4:
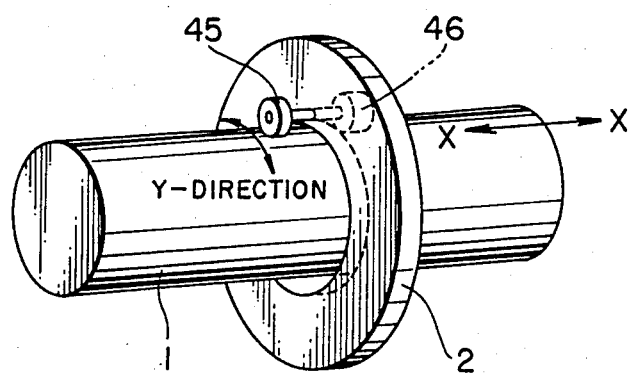
FIG. 4 shows, in perspective view, another example of the snaking prevention sensor.

FIG. 4 shows another embodiment of the snaking prevention sensor 4. A detection wheel 45 for snaking prevention has a shaft supported in a direction of arrow X—X (axial direction of the pipe 1) and detects a circumferential rotation (Y-direction) of the scanner base 2 which in turn is converted into an electrical signal by means of an encoder 46.

Figure 5:
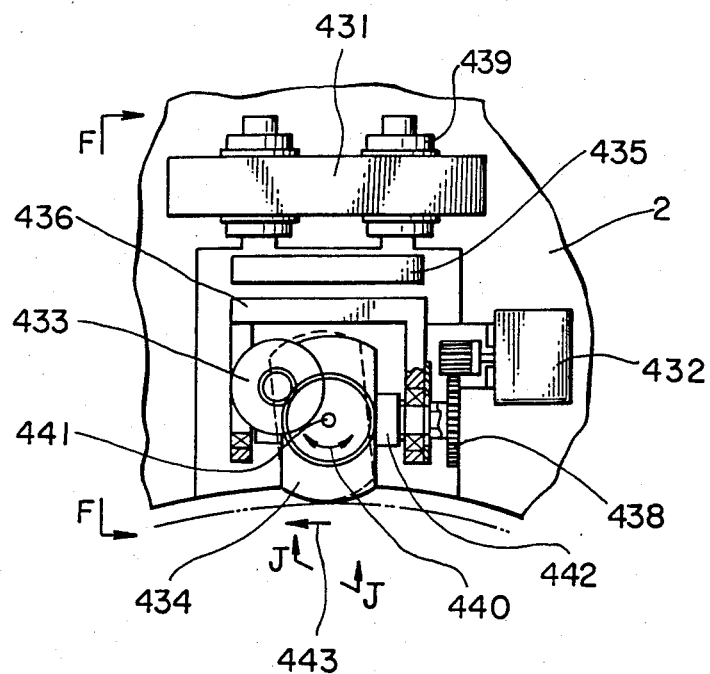
FIG. 5 is a fragmentary sectional view showing still another example of the snaking prevention sensor.
Figure 6:
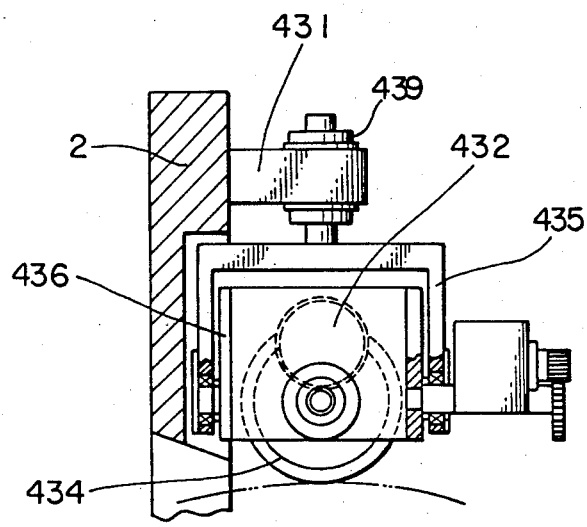
FIG. 6 is a sectional view as seen from an arrow F—F in FIG. 5.
Figure 7:
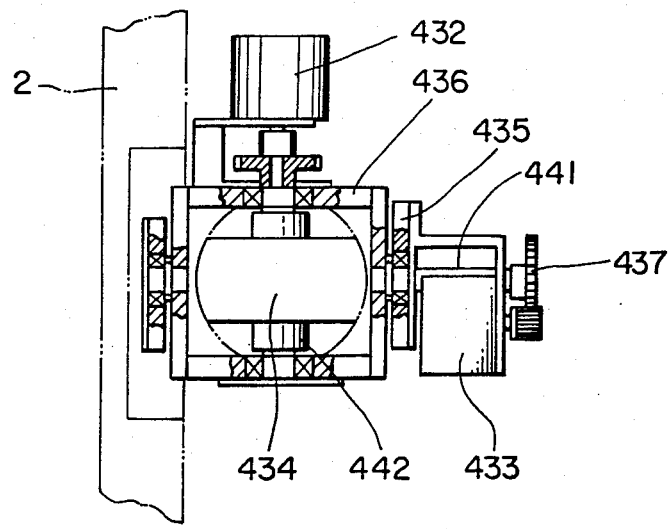
FIG. 7 is a similar view as seen from an arrow J—J.

FIG. 5 shows a third embodiment of the snaking prevention sensor which is depicted in FIG. 6 as viewed from an arrow F—F and in FIG. 7 as viewed from an arrow J—J. The snaking prevention sensor 4 in this embodiment comprises a snaking detection wheel 434 being in contact with the pipe 1, a box 436 supporting the snaking detection wheel 434 through wheels 442, a channel 435 supporting the box 436 through a shaft 441, and a fixture plate 431 fixed to the base and to which the channel 435 is secured by means of threaded shafts 439. The box 436 is pivotal about the shaft 441 in directions of arrow 440 and with respect to the channel 435 fixed to the base 2. Accordingly, when the scanner makes a snaking motion circumferentially of the pipe 1 in a direction of arrow 443, the snaking detection wheel 434 is inclined as shown at dotted line. An amount of inclination is detected by an encoder 433 fixed to the channel 435 through a gear train 437, thus providing an amount of circumferential turning of the scanner. In addition, an amount of rotation of the snaking detection wheel 434 is also detected through a gear 438 by means of an encoder 432 fixed to the channel 435, so that a position of the scanner referenced to a start point or a reference point can be measured as in the first embodiment by integrating the detected rotation amounts. When the output of each of the encoders 48, 46 and 433 providing outputs of the snaking prevention sensors 4 in the foregoing three embodiments is indicated by $\phi$, the scanner can be prevented from being deviated or turned circumferentially of the pipe 1 by controlling the output $\phi$ to zero. This can be implemented with an arrangement specified as the circumferential posture control mechanism 5 responsive to the output of the snaking prevention sensor 4.

Figure 8:
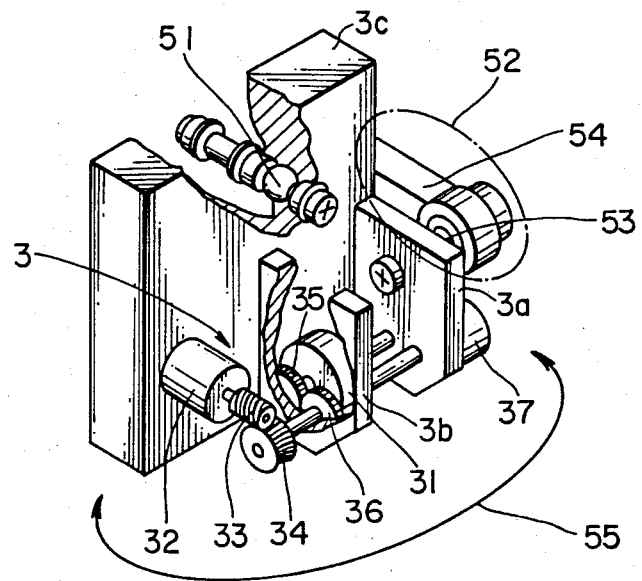
FIG. 8 is a perspective view illustrating an example of a circumferential posture control mechanism.

FIG. 8 shows an embodiment of the circumferential posture control mechanism 5 which comprises a ball joint 51 fixed to the base 2 and to which the mount plate 3c is pivotally mounted to swing in directions of arrow 55, and a solenoid assembly 52. The solenoid assembly 52 has a movable plunger 53 fitted in the mount plate 3a of the axial running unit, and a stationary portion 54 fixed to the base 2. The movable plunger 53 can be projected or retracted in dependence on the direction of current passed through the stationary portion 54. The current direction is determined by the output of the snaking prevention sensor 4. Thus, if the solenoid assembly 52 is set such that its projected or retracted movable plunger 53 causes the axial running unit 3 directed straighforwardly to turn to the rightward or leftward direction, then the drive wheel 31 will follow the axial running unit 3 to control its direction correspondingly, thereby controlling the circumferential posture of the scanner. When this posture control is applied to the plurality of drive wheels 31 simultaneously, these drive wheels 31 should be controlled so as to be directed in the same direction.

Figure 9:
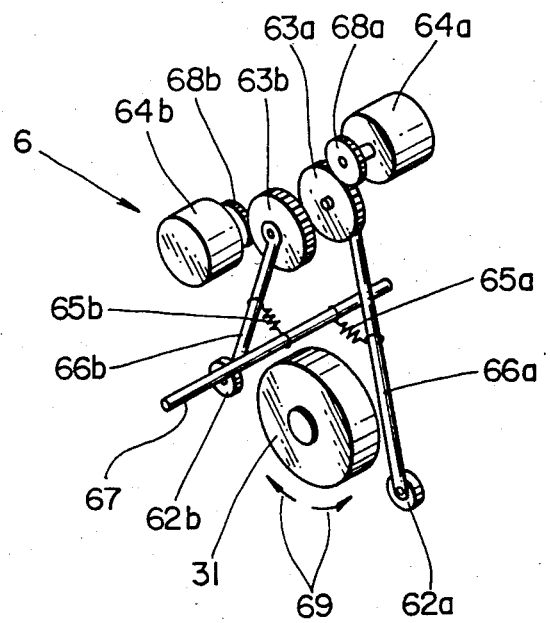
FIG. 9 is a perspective view showing an example of a curvature sensor.
Figure 10:
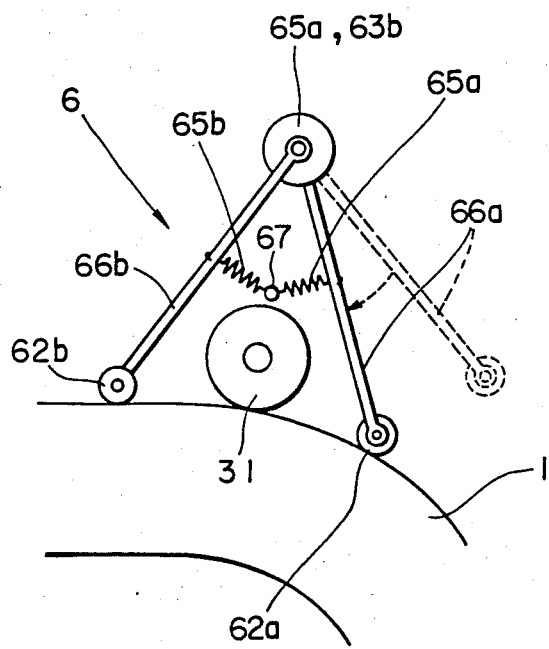
FIG. 10 is a front view of the curvature sensor.

An embodiment of the curvature sensor 6 is shown, in perspective view, in FIG. 9 and its front view is shown in FIG. 10. In this emboidment, the sensor 6 consists of two sets of symmetrical sub-sensors. Reference numerals representing members of one set are suffixed with "a" and those representing members of the other set are suffixed with "b".

In either sub-sensor, an arm 66 has at one end a rotatably mounted wheel 62 and at the other end a fixedly mounted gear 63. The arm 66 is normally tensioned by a spring 65 applied between the arm 66 and a stationary bar 67 supported by the mount plates 3a and 3b of the axial running unit. As the scanner preceeds, for example, from a straight pipe portion to a curved pipe portion as shown in FIG. 10, the arm 66a is pulled by the spring 65a from a position depicted by dotted line to another position depicted by solid line to rotate the gear 63a. Then, an amount of rotation is amplified by an acceleration gear 68a and detected by an absolute encoder 64a. One sub-sensor preceeds the drive wheel 31 and the other sub-sensor succeeds it. The other sub-sensor suffixed with "b" operates similarly to but independently of one sub-sensor suffixed with "a". Assuming now that the absolute encoder 64a or 64b generates a positive output when the arm 66a or 66b normally tensioned toward the stationary bar 67 is moved in a direction of arrow 69, the rotation speed of the drive wheel 31 is controlled such that $\epsilon_\theta$ in equation (1) is made zero, thereby bringing the scanner into posture normal to the pipe 1.

$$\epsilon_\theta = \theta_a - \theta_b \qquad (1)$$

where $\theta_a$ represents an output amount of the absolute encoder 64a, and $\theta_b$ an output amount of the absolute encoder 64b.

A curvature of the curved pipe portion can be measured by using either one output or an averaged output of the absolute encoder 64a and 64b.

Figure 11:
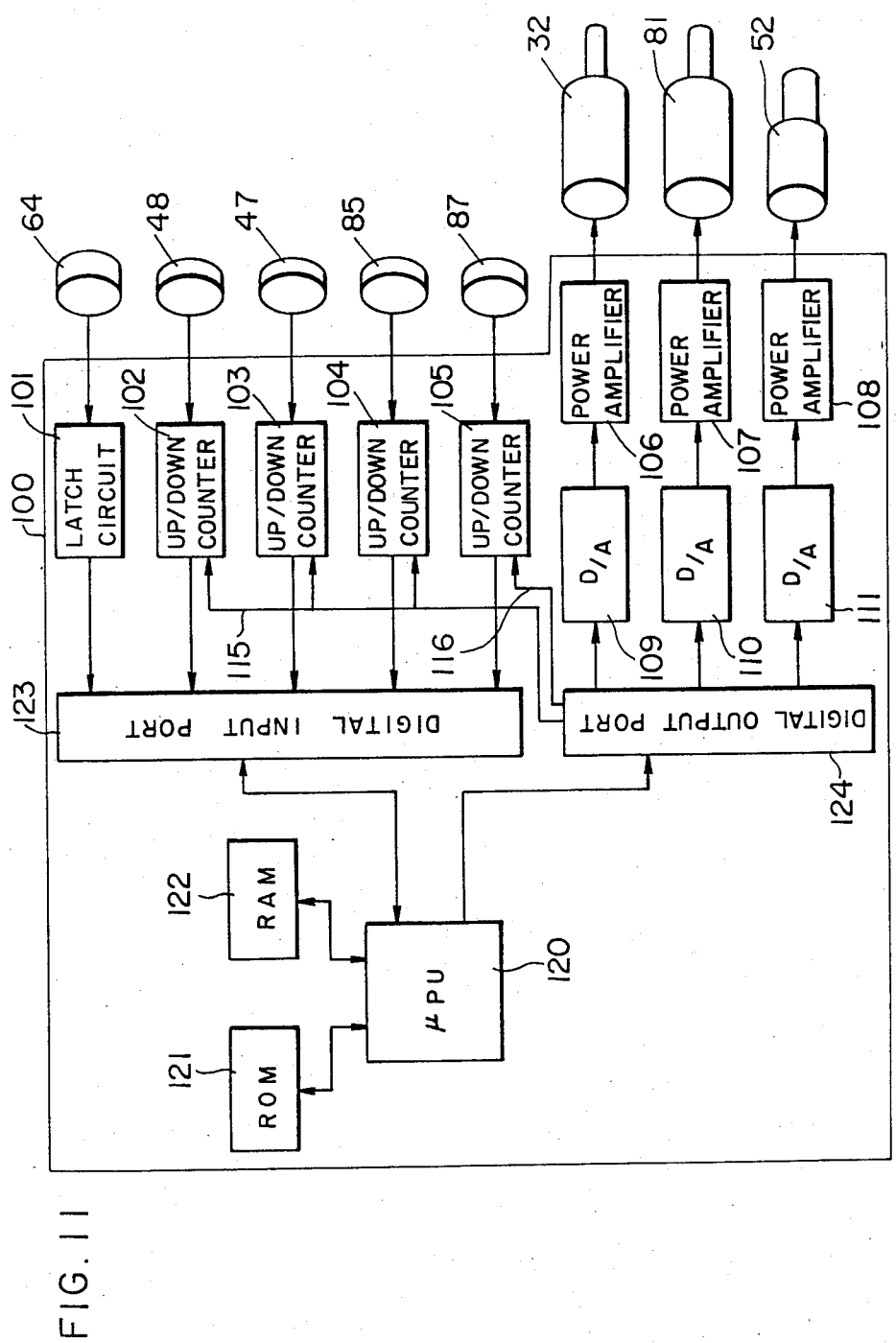
FIG. 11 is a schematic block diagram of a controller.

A controller 100 for the operation of the scanner is configured as shown in FIG. 11. A digital input port 123 receives the output signals from six absolute encoders 64 of the curvature sensors 6 mounted to the respective axial running units via a latch circuit 101, the output signal from the encoder 48 of the snaking prevention sensor 4 via an up/down counter 102, the output signal from the axial travel distance detecting encoder 47 via an up/down counter 103, the output signal from the circumferential rotor position detecting encoder 85 via an up/down counter 104, and the output signal from the axial drive motor speed detecting encoder 37 via an up/down counter counter 105. These output signals thus received by the digital input port 123 are fetched by a microprocessor unit ($\mu$PU) 120 and stored in a RAM 122. The snaking prevention control and the posture control necessary for stable travel even along curved pipe portions are carried out in accordance with programs written in a ROM 121 by using the thus detected data. Operation quantities determined by respective programs are sent to a digital output port 124, converted by D/A converters 109 to 111 into analog quantities, power-amplified by power amplifiers 106 to 108, and finally applied to actuators including axial drive motor 32, circumferential drive motor 81 and solenoid assembly 52. Signals 115 and 116 are used as reset signals for the up/down counters 102 to 105. The reset signal 115 is produced at a reference position such as a weld end and an inspection start point to be described later. The reset signal 116, on the other hand, is produced immediately after reading data at the rate of a sampling period standing for a control period.

Figure 12:
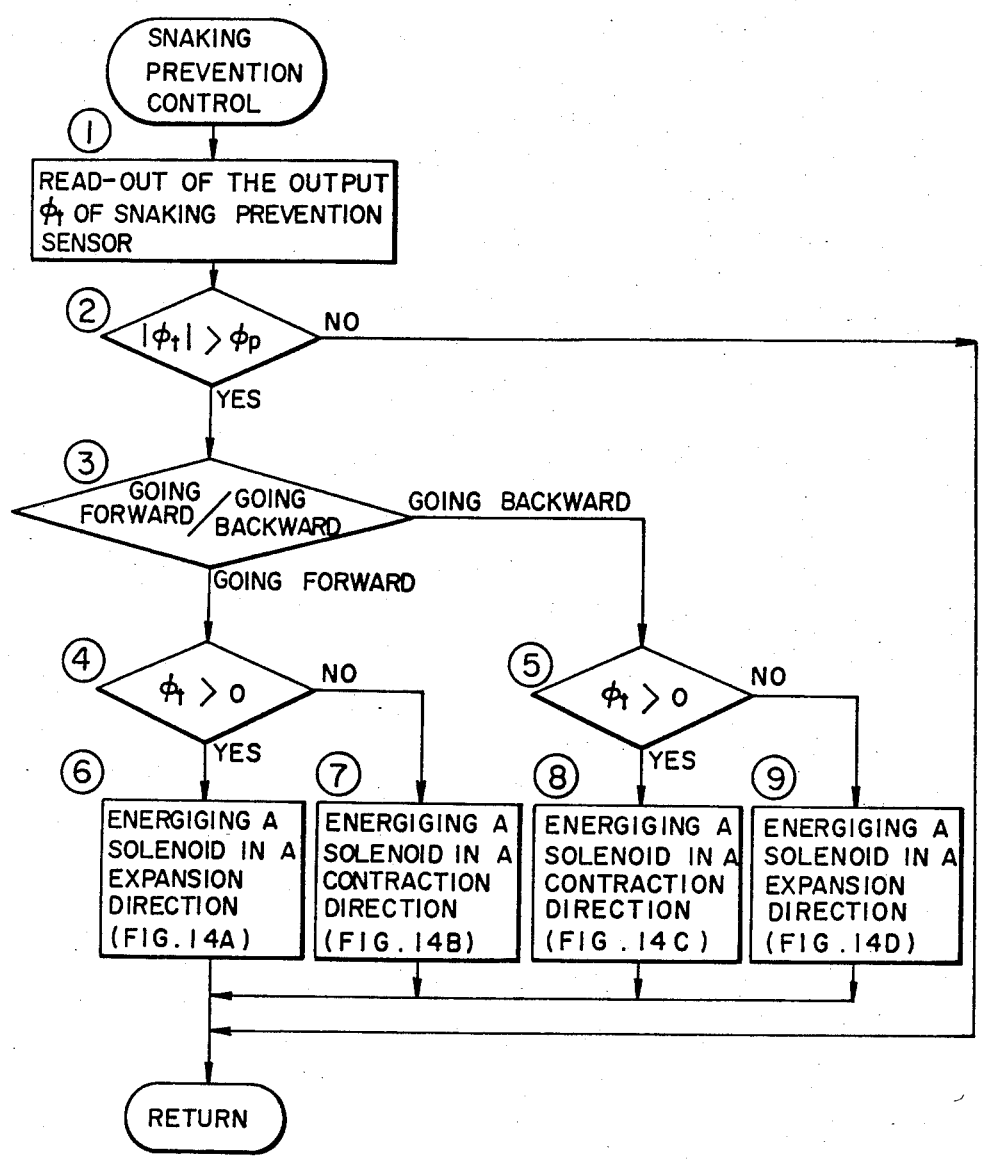
FIG. 12 is a flow chart useful in explaining snaking prevention control.
Figure 13:
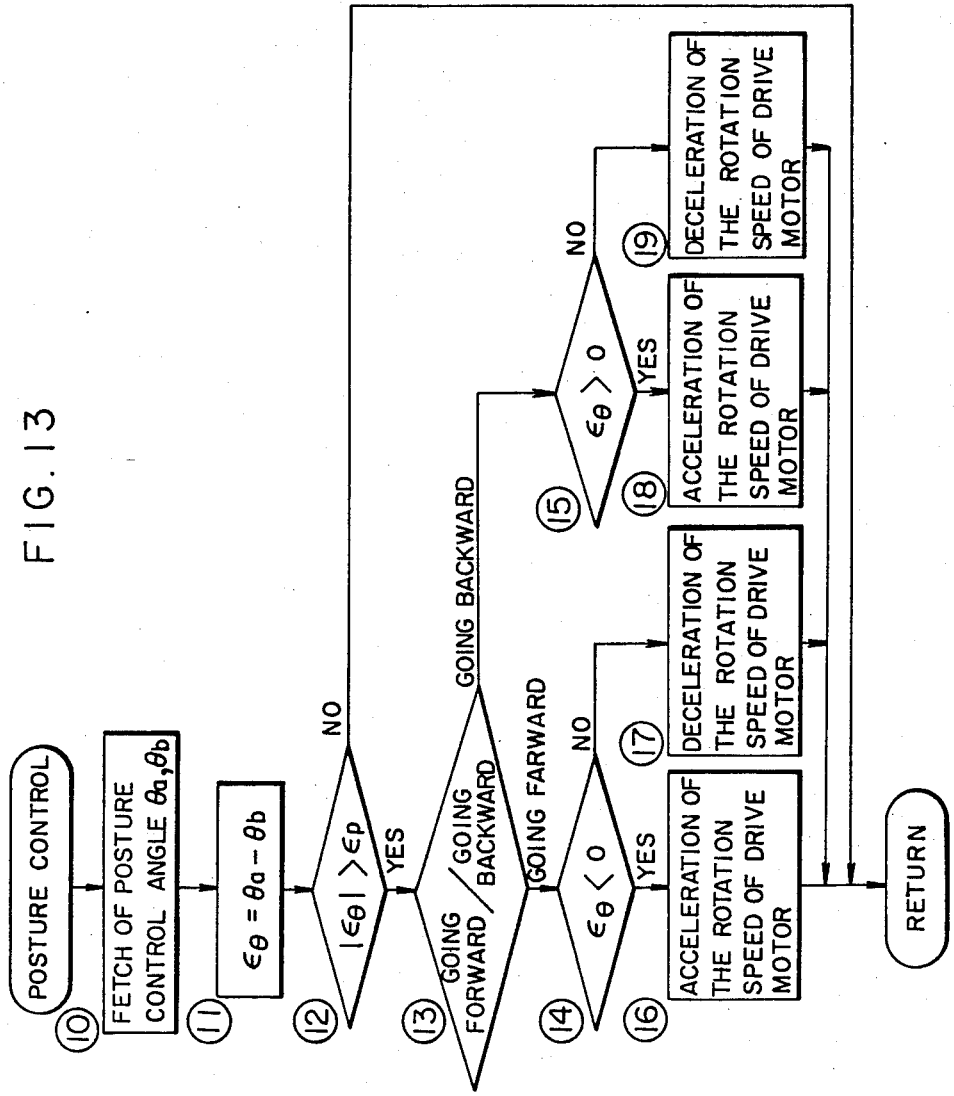
FIG. 13 is a flow chart for posture control.

Programs written in the ROM 121 are exemplified in terms of flow charts as shown in FIGS. 12 and 13. A flow chart of FIG. 12 is for snaking prevention control and a flow chart of FIG. 13 is for posture control.

Figure 14A:
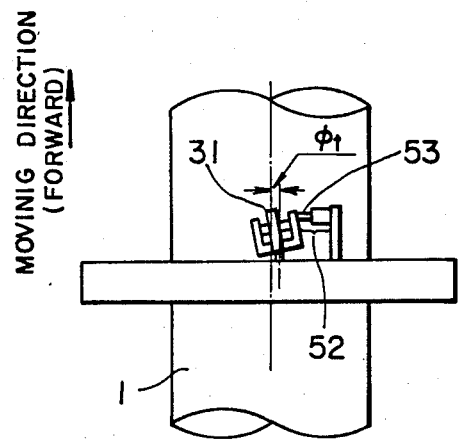
FIGS. 14A to 14D are diagrams illustrating solenoid operations controlled for four different types of snaking control.
Figure 14B:
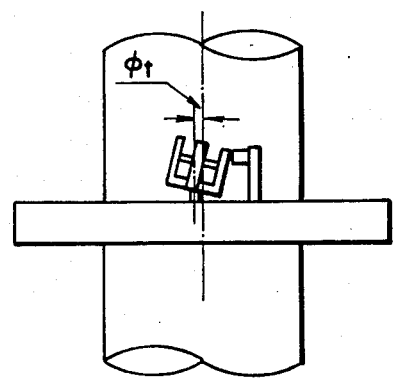
Figure 14C:
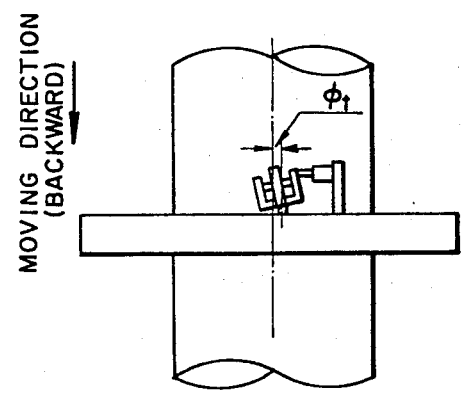
Figure 14D:
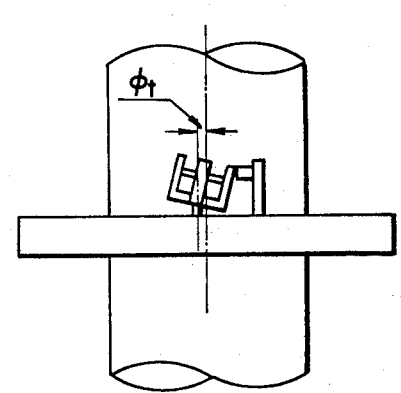

The snaking prevention control will first be described. When the program starts, the $\mu$PU 120 first reads an output signal $\Psi_t$ of the snaking prevention sensor (step 1), and it is judged whether an absolute value of the output signal $\Psi_t$ is larger than an allowable value $\Psi_p$ (step 2). If "NO", the controlling is not modified and continues to "return". If "YES", the solenoid of the circumferential posture control mechanism 5 is controlled in dependence on the travelling or moving direction of the scanner and the polarity of the output signal $\Psi_t$ (steps 3 to 9). This controlling will be described more specifically by also referring to FIGS. 14A to 14D which illustrate four different states wherein the solenoid needs to be controlled. FIG. 14A shows a case where the scanner deviates rightwards in the circumferential direction $\Psi_t$ is positive for rightward deviation) during its forward going. Since in this case the scanner needs to be turned to the left, the movable plunger 53 of the solenoid assembly 52 is projected so as to steer the drive wheel 31 leftwards. FIG. 14B shows a case where the scanner deviates leftwards in the circumferential direction during its forward going. In this case, the movable plunger 53 is retracted to steer the drive wheel rightwards. In addition to the controlling of the scanner during its forward going, the scanner will be controlled during its backward going as illustrated in FIGS. 14C and 14D. Specifically, it will be appreciated that the movable plunger 53 of the solenoid is moved in opposite directions to those for the forward going in dependence on the polarities of the output signal $\Psi_t$ from the snaking prevention sensor.

Figure 15A:
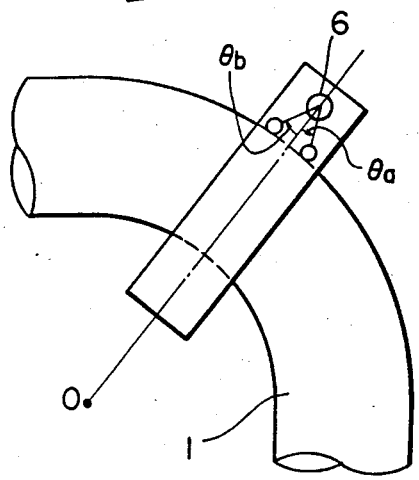
FIGS. 15A to 15C show three different kinds of posture of the scanner.
Figure 15B:
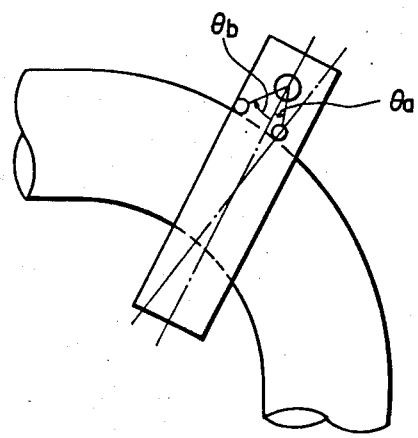
Figure 15C:
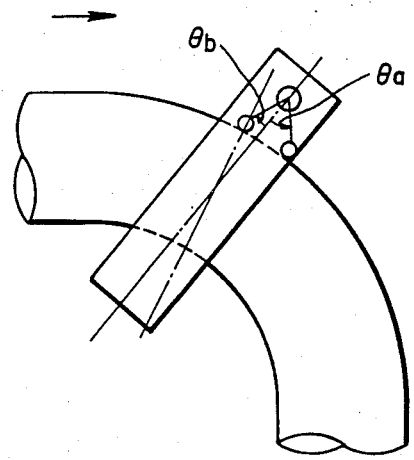

The posture control will now be described with reference to a flow chart of FIG. 13. The curvature sensors 6 for posture control are each provided for each of the three drive wheels spaced at 120° intervals. Since the respective drive wheels can be controlled independently if speed of each axial drive motor 32 for driving each drive wheel 31 is controlled within an allowable load range, the posture control associated with only one drive wheel will be described in the following. When the program starts, the $\mu$PU 120 fetches posture control angles $\theta_a$ and $\theta_b$ delivered out of the curvature sensor 6 (step 10), and a difference $\epsilon_\theta$ is calculated (step 11). It is judged whether the difference $\epsilon_\theta$ is larger than an allowable value $\epsilon_p$ (step 12). If "NO", the speed of the drive wheel 31 is not corrected and the drive wheel 31 continues to rotate. If "YES", acceleration or deceleration of the rotation speed of the drive wheel 31 is decided in dependence on the moving direction of the scanner and the polarity of $\epsilon_\theta$ (steps 13 to 19). FIGS. 15A to 15C illustrate three kinds of posture of the scanner relative to the pipe 1 during forward going of the scanner. Specifically, FIG. 15A shows a case where the scanner is postured normal to the pipe 1, indicating that the running speed of the drive wheel 31 is balanced. FIG. 15B shows a case where the scanner is so postured, relative to the pipe 1, as to be inclined backwards, indicating that the rotation speed of one drive wheel 31 in question is lower than that of the other drive wheels. FIG. 15C shows a case where, in contrast to the case of FIG. 15B, the scanner is so postured as to be inclined forwards in relation to the pipe 1, indicating that the rotation speed of the drive wheel in question is higher than that of the other drive wheels. Accordingly, in order to bring the state of FIGS. 15B and 15C into the posture of FIG. 15A, the rotation speed of the drive wheel is accelerated to correct the state of FIG. 15B (step 16) or conversely the rotation speed is decelerated to correct the state of FIG. 15C (step 17). During backward going of the scanner, the precedence of $\theta_a$ relative to $\theta_b$ is reversed and hence the acceleration/deceleration of the rotation speed dependent on polarities of $\epsilon_\theta$ is reversed to that for the forward going (steps 18 to 19). In this manner, the posture of the scanner can be controlled in accordance with the control flow of FIG. 13 to constantly keep the scanner normal to the pipe 1.

Figure 16:
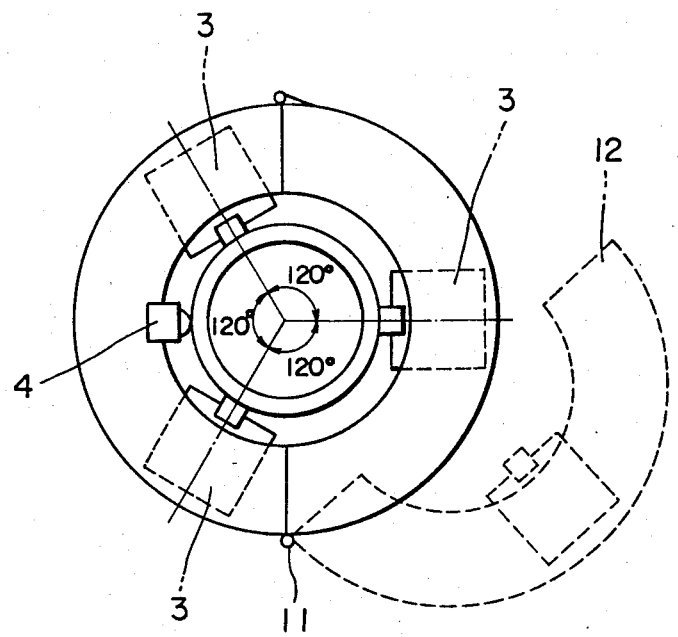
FIG. 16 is a front view of a base mounting/dismounting mechanism.

The base 2 provided with the axial running unit 4 and the circumferential rotor 7 with the ultrasonic probe fixed thereto may be halved and may be provided with a mating mechanism adapted to put together these halves. An embodiment of the halved base 2 is illustrated in FIG. 16. The base 2 has a hinge 11 and a hook 12. When the hook 12 is released, the half of the base can be opened about the hinge 11 to ensure easy removal of the base from the pipe.

The construction of the foregoing embodiments along with the operation of their constituents have been described hereinbefore. The scanner will be used in a manner as exemplified below.

The base 2 provided with the axial running unit 3 and the like is first mounted to the pipe 1 standing for an object to be examined and then the circumferential rotor 7 provided with the ultrasonic probe 91 and the like is fixed to the base 2. The controller (FIG. 11) consisting of, for example, a microcomputer controls the scanner as follows:

(1) The scanner is caused to move back and forth and the speed of each drive wheel 31 is controlled pursuant to equation (1) so that the scanner can be postured normal to the pipe 1.

(2) The scanner is travelled toward a welded area, and one edge of the welded area is detected by the ultrasonic probe 91. The edge position is used as a reference point.

(3) The scanner is returned to one edge of a non-destructive examination area extending beyond the welded area, and the examination is started. A non-destructive examination is continued until the scanner reaches the other edge of the examination area.

(4) If necessary, the scanner is moved to the next welded area, and the operations described in items (2) and (3) above are repeated.

Figure 17:
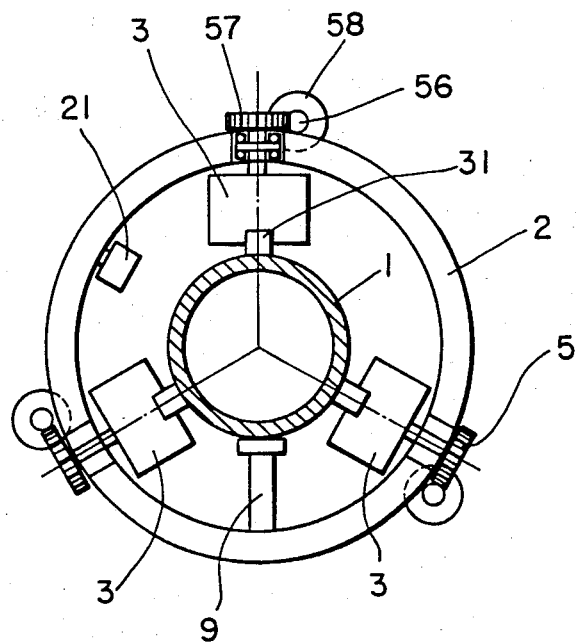
FIG. 17 is a front view showing another embodiment of the circumferential posture control mechanism.

To describe further embodiments, FIG. 17 illustrates another embodiment of the circumferential posture control mechanism 5. In this embodiment, the entire axial running unit 3 is permitted to swing with respect to a center point at which the drive wheel 31 grounds on the pipe 1 by means of a circumferential posture control motor 58, an input worm gear 56 and an output worm gear 57. Since in this embodiment the three drive wheels 31 can be controlled from the axial direction to the circumferential direction, the circumferential rotor 7 and circumferential rotor drive mechanism 8 can be dispensed with, thereby making it possible to conduct examination in the circumferential direction even by using a ultrasonic probe mechanism 9 directly mounted to the base 2.

Figure 18:
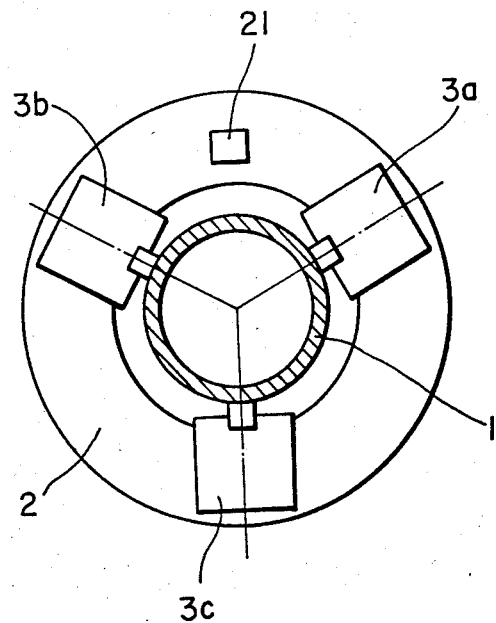
FIG. 18 is a diagram for explaining the scanner subject to symmetrical posture control with respect to its axis.

As far as the scanner is mounted to a horizontally laid piping, the scanner can be controlled so as to be postured desirably even in the circumferential direction by using a gravity sensor such as a level 21 mounted to the base 2 as shown in FIG. 18 in combination with the aforementioned circumferential posture control mechanism 5. This arrangement is therefore advantageous in the following two points:

(a) Since, upon mounting, the scanner can be controlled so as to be postured symmetrically as shown in FIG. 18, the subsequent travel control, especially along a curved pipe portion, including the posture control effected by the use of the snaking prevention sensor 4 and curvature sensor 6 can be simplified. This is because speed command values for the drive wheels 3a and 3b can be made substantially identical and because torque variations of the aixal drive motor 32 can be reduced when the posture of the scanner is controlled during travelling along horizontally laid pipings such that the drive wheels 3a and 3b, for example, support gravity of the scanner. Thanks to the reduction in torque variations a motor can be chosen which is compatible with reduction of size and weight of the scanner.

(b) An absolute position can be detected in the circumferential direction and hence a non-destructive examination position can be acquired properly.

Figure 19:
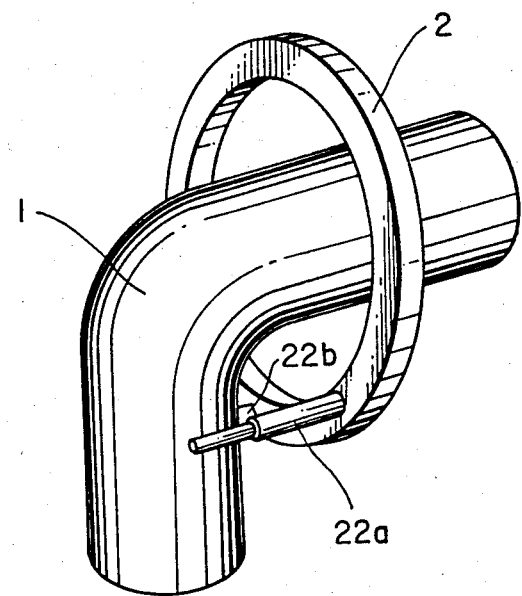
FIG. 19 is a perspective view showing a circumferential posture sensor in engagement with a vertical pipe near an elbow.

FIG. 19 shows an example of a circumferential posture sensor in engagement with a vertical pipe near an elbow. Two telescopic contact sensors 22a and 22b, which terminate in ball-like tips, extend axially from the base 2. When the circumferential posture of the scanner is controlled by using the circumferential posture control mechanism 5 so that the two contact sensors 22a and 22b are equidistant, the scanner can be controlled so as to be postured symmetrically as shown in FIG. 18.

We claim:

1. A trackless scanner for examination of pipings comprising:
   an annular base removably mountable to a pipe to be examined;
   a plurality of drive wheels for running supported on said base and being in contact with said pipe;
   a sensor, associated with each drive wheel, for detecting a circumferential turning of said base relative to said pipe;
   a circumferential posture control mechanism, associated with each drive wheel, responsive to a detection signal from said sensor so as to control an axial running of said drive wheel; and
   a sensor, associated with each drive wheel, for detecting a curvature of said pipe.

2. A trackless scanner for piping examination according to claim 1 further comprising an annular circumferential rotor rotatably mounted to said base concentrically therewith;
   rotation drive means for rotating said annular circumferential rotor relative to said base; and
   a sensor for piping examination mounted on said circumferential rotor.

3. A trackless scanner for piping examination according to claim 2 wherein said sensor for detection of the circumferential turning comprises:
   a ball member being in slidable contact with said pipe and free to rotate; and
   means for detecting a rotation amount of said ball member in terms of components on two orthogonal axes.

4. A trackless scanner for piping examination according to claim 2 wherein said sensor for detection of the circumferential turning comprises:
   a wheel rotatably supported on a shaft extending in parallel with a center axis of said annular base and being in slidable contact with said pipe to be examined; and
   means for detecting a rotation amount of said wheel.

5. A trackless scanner for piping examination according to claim 2 wherein said curvature sensor comprises a plurality of sub-sensors, each sub-sensor including:
   a rotatably supported arm;
   a wheel rotatably mounted to one end of said arm and being in slidable contact with said pipe near said drive wheel; and
   means, provided on the other end of said arm, for detecting a rotation angle of said arm.

6. A trackless scanner for piping examination according to claim 1 wherein said circumferential posture control mechanism comprises:
   means for rotatably supporting a mount plate member of said drive wheel relative to said base; and
   means for rotating said mount plate member relative to said base.

7. A trackless scanner for piping examination according to claim 6 wherein said sensor for detection of the circumferential turning comprises:
   a ball member being in slidable contact with said pipe and free to rotate; and means for detecting a rotation amount of said ball member in terms of components on two orthogonal axes.

8. A trackless scanner for piping examination according to claim 6 wherein said sensor for detection of the the circumferential turning comprises:
 a wheel rotatably supported on a shaft extending in parallel with a center axis of said annular base and being in slidable contact with said pipe to be examined; and
 means for detecting a rotation amount of said wheel.

9. A trackless scanner for piping examination according to claim 6 wherein said curvature sensor comprises a plurality of sub-sensors, each sub-sensor including:
 a rotatably supported arm;
 a wheel rotatably mounted to one end of said arm and being in slidable contact with said pipe near said drive wheel; and
 means, provided on the other end of said arm, for detecting a rotation angle of said arm.

10. A trackless scanner for piping examination according to claim 6 wherein said circumferential posture control mechanism uses a gravity sensor for detecting the direction of the force of gravity.

11. A trackless scanner for piping examination according to claim 1 wherein said sensor for detection of the circumferential turning comprises:
 a ball member being in slidable contact with said pipe and free to rotate; and
 means for detecting a rotation amount of said ball member in terms of components on two orthogonal axes.

12. A trackless scanner for piping examination according to claim 1 wherein said sensor for detection of the circumferential turning comprises:
 a wheel rotatably supported on a shaft extending in parallel with a center axis of said annular base and being in slidable contact with said pipe to be examined; and
 means for detecting a rotation amount of said wheel.

13. A trackless scanner for piping examination according to claim 1 wherein said curvature sensor comprises a plurality of sub-sensors, each sub-sensor including:
 a rotatably supported arm;
 a wheel rotatably mounted to one end of said arm and being in slidable contact with said pipe near said drive wheel; and
 means, provided on the other end of said arm, for detecting a rotation angle of said arm.

14. A trackless scanner for piping examination according to claim 1 wherein said circumferential posture control mechanism uses a gravity sensor for detecting the direction of the force of gravity.

* * * * *